United States Patent
Kawanami et al.

(10) Patent No.: US 10,179,755 B2
(45) Date of Patent: Jan. 15, 2019

(54) METHOD FOR PREPARING BRANCHED ALCOHOL

(71) Applicants: NATIONAL INSTITUTE OF ADVANCED INDUSTRIAL SCIENCE AND TECHNOLOGY, Tokyo (JP); NISSAN CHEMICAL INDUSTRIES, LTD., Tokyo (JP)

(72) Inventors: Hajime Kawanami, Sendai (JP); Takayuki Ishizaka, Sendai (JP); Hitomi Fujiyama, Sendai (JP); Nobuyuki Kakiuchi, Funabashi (JP); Norihito Shiga, Funabashi (JP)

(73) Assignees: NATIONAL INSTITUTE OF ADVANCED INDUSTRIAL SCIENCE AND TECHNOLOGY, Tokyo (JP); NISSAN CHEMICAL INDUSTRIES, LTD., Tokyo (JP)

( * ) Notice: Subject to any disclaimer, the term of this patent is extended or adjusted under 35 U.S.C. 154(b) by 0 days.

(21) Appl. No.: 15/577,651

(22) PCT Filed: May 27, 2016

(86) PCT No.: PCT/JP2016/065688
§ 371 (c)(1),
(2) Date: Nov. 28, 2017

(87) PCT Pub. No.: WO2016/194800
PCT Pub. Date: Dec. 8, 2016

(65) Prior Publication Data
US 2018/0162796 A1 Jun. 14, 2018

(30) Foreign Application Priority Data
May 29, 2015 (JP) ................ 2015-109390

(51) Int. Cl.
*C07C 29/34* (2006.01)
*C07C 31/125* (2006.01)
*B01J 31/02* (2006.01)

(52) U.S. Cl.
CPC ........... *C07C 29/34* (2013.01); *B01J 31/0207* (2013.01); *C07C 31/125* (2013.01)

(58) Field of Classification Search
CPC ........ C07C 29/34; C07C 31/125; C07B 61/00
See application file for complete search history.

(56) References Cited

U.S. PATENT DOCUMENTS

| 1,992,480 A | * | 2/1935 | Fuchs | C07C 29/34 |
| | | | | 568/905 |
| 4,792,620 A | * | 12/1988 | Paulik | B01J 31/0231 |
| | | | | 560/232 |
| 6,419,797 B1 | | 7/2002 | Scherf et al. | |
| 8,318,990 B2 | | 11/2012 | Tanaka et al. | |

FOREIGN PATENT DOCUMENTS

| JP | 49035308 A | * | 4/1974 |
| JP | 02-180853 A | | 7/1990 |
| JP | 2001-513521 A | | 9/2001 |
| JP | 2004-300111 A | | 10/2004 |
| JP | 2005-131527 A | | 5/2005 |
| JP | 2009-167183 A | | 7/2009 |
| WO | WO 91/04242 A1 | | 4/1991 |

OTHER PUBLICATIONS

Norskov et al, Nature Chemistry, Towards the Computational Design of Solid Catalysts, 2009, 1, pp. 37-46. (Year: 2009).*
Burk, Journal of Molecular Catalysis, The Rhodium-promoted Guerbet Reaction Part I. Higher Alcohols from Lower Alcohols, 1985, 33 pp. 1-14 (Year: 1985).*
Burk et al., "The Rhodium-Promoted Guerbet Reaction Part I. Higher Alcohols from Lower Alcohols", Journal of Molecular Catalysis, 1985, vol. 33, pp. 1-14.
Gryglewcz et al., "Synthesis of Modern Synthetic Oils Based on Dialkyl Carbonates", Industrial & Engineering Chemistry Research, 2003, vol. 42, pp. 5007-5010.
International Search Report for PCT/JP2016/065688 (PCT/ISA/210) dated Aug. 23, 2016.
Kozlowski et al., "Heterogeneous Catalysts for the Guerbet Coupling of Alcohols", ACS Catalysis, 2013, vol. 3, pp. 1588-1600.
Written Opinion of the International Searching Authority for PCT/JP2016/065688 (PCT/ISA/237) dated Aug. 23, 2016.

* cited by examiner

*Primary Examiner* — Paul A Zucker
(74) *Attorney, Agent, or Firm* — Birch, Stewart, Kolasch & Birch, LLP

(57) ABSTRACT

A method for preparing a branched alcohol by dimerizing an aliphatic monoalcohol having three or more carbon atoms in the presence of a base and a catalyst. The dimerization reaction is performed under atmospheric pressure while injecting a hydrogen gas. With this method, it is possible to obtain a dimerized alcohol with excellent yield even when using a branched aliphatic monoalcohol as the starting material.

20 Claims, No Drawings

METHOD FOR PREPARING BRANCHED ALCOHOL

TECHNICAL FIELD

The present invention relates to a method for preparing branched alcohol, and more specifically to a method for preparing branched alcohol using the Guerbet reaction.

BACKGROUND ART

The Guerbet reaction has hitherto been known as a method for preparing a branched alcohol by dimerizing an aliphatic monoalcohol.

Generally, this reaction is thought to proceed by the combination of a mechanism that involves the abstraction of hydrogen from a starting alcohol in the presence of a basic compound and a catalyst (hydrogen transfer reaction) to form the corresponding aldehyde intermediate, a mechanism in which the aldehyde intermediate is dimerized via aldol condensation to form an $\alpha,\beta$-unsaturated aldehyde intermediate, and a mechanism in which hydrogen is added to the $\alpha,\beta$-unsaturated aldehyde intermediate (Hydrogen transfer reaction) to form an alcohol (see, for example, Non-Patent Document 1).

It is known that the Guerbet reaction proceeds at a relatively good yield when a linear alcohol is used as the starting material, but that the yield of the target compound tends to decrease when a branched alcohol is used as the starting material, perhaps on account of a decrease in reactivity due to steric hindrance by the branched alcohol.

Were it possible to improve the yield here, this would lead to a large reduction in production costs. Hence, improving the yield of the Guerbet reaction is an important concern in terms of establishing an industrial production process.

PRIOR ART DOCUMENTS

Patent Documents

Patent Document 1: JP-A 2009-167183

Non-Patent Documents

Non-Patent Document 1: ACS Catalysis, 2013, 3, 1588-1600

SUMMARY OF THE INVENTION

Problems to be Solved by the Invention

It is therefore an object of the present invention to provide a method for preparing branched alcohol which is capable of obtaining a dimerized alcohol in a good yield even when a branched aliphatic monoalcohol is used as the starting material.

Means for Solving the Problems

The inventors have conducted extensive investigations in order to achieve the above object. As a result, they have discovered that by carrying out a Guerbet reaction while blowing hydrogen into the reaction system, the reaction proceeds in a good yield not only with a linear alcohol, but even when a branched alcohol is used as the starting material.

Patent Document 1 discloses a technique which, when dimerizing an alcohol having four or fewer carbon atoms by the Guerbet reaction, effects the reaction under hydrogen pressurization within an autoclave. However, this prior art discloses neither a technique that blows in hydrogen within an open system nor the advantages of such a technique.

Accordingly, the invention provides:
1. A method for preparing branched alcohol, which method includes the step of subjecting an aliphatic monoalcohol having at least three carbon atoms to a dimerizing reaction in the presence of a base and a catalyst, wherein the dimerizing reaction is carried out under atmospheric pressure and while blowing in hydrogen gas;
2. The branched alcohol preparation method of 1 above, wherein the aliphatic monoalcohol is an aliphatic monoalcohol having five or more carbon atoms;
3. The branched alcohol preparation method of 2 above, wherein the aliphatic monoalcohol is an aliphatic monoalcohol having eight or more carbon atoms;
4. The branched alcohol preparation method of 2 or 3 above, wherein the aliphatic monoalcohol is a branched aliphatic monoalcohol;
5. The branched alcohol preparation method of 3 above, wherein the aliphatic monoalcohol is 1-octanol, 1-decanol or 3,5,5-trimethyl-1-hexanol;
6. The branched alcohol preparation method of 4 above, wherein the branched aliphatic monoalcohol is 3,5,5-trimethyl-1-hexanol;
7. The branched alcohol preparation method of any one of 1 to 6 above, wherein the reaction is carried out while removing water that forms in the dimerization reaction;
8. The branched alcohol preparation method of any one of 1 to 7 above, wherein the catalyst is a metal oxide;
9. The branched alcohol preparation method of any one of 1 to 7 above, wherein the catalyst is an aliphatic aldehyde; and
10. The branched alcohol preparation method of 9 above, wherein the aliphatic aldehyde is an aldehyde having a skeleton and a number of carbon atoms corresponding to the aliphatic monoalcohol.

Advantageous Effects of the Invention

The method for preparing branched alcohol of the invention is able to improve the yield of dimerized alcohol by the Guerbet reaction. The inventive method is especially effective when a branched aliphatic alcohol is used as the starting material.

The reason for this increase in yield is not clear, although one factor is thought to be that, by blowing in hydrogen gas, the final hydrogenation mechanism proceeds smoothly and the rate of the reaction increases even when a highly branched starting material is used. Another factor is thought to be that, because the reducing conditions of a hydrogen atmosphere are used, there is little by-product acid, increasing the yield.

Because the method of the invention does not require conditions such as hydrogen pressurization and moreover has an increased yield, the burden of distillation and purification is reduced. Hence, this is an industrially beneficial process that is suitable for large-scale production.

EMBODIMENT FOR CARRYING OUT THE INVENTION

The invention is described more fully below.

The inventive method for preparing branched alcohol is characterized by, in the production of a branched alcohol by subjecting an aliphatic monoalcohol having at least three carbon atoms to a dimerizing reaction in the presence of a base and a catalyst, carrying out the dimerizing reaction under atmospheric pressure and while blowing in hydrogen gas.

In the invention, the hydrogen gas blowing rate is not particularly limited and may be set to, for example, about 0.05 to 25 L/min per mole of the monoalcohol. However, taking into account the balance between the amount of hydrogen used and the reaction yield, the rate is preferably from about 0.05 to about 5 L/min, more preferably from about 0.05 to about 2.5 L/min, and even more preferably from about 0.25 to about 1 L/min.

Any method may be used to blow in hydrogen, such as the method of inserting a blowing tube into the reaction mixture and bubbling through hydrogen gas.

The aliphatic monoalcohol used as the starting material is not particularly limited, so long as it is a primary or secondary alcohol having three or more carbon atoms, although a primary alcohol is preferred. The lower limit in the number of emboli atoms is preferably at least five, and more preferably at least eight. The upper limit in the number of carbon atoms is preferably 20 or less, and more preferably 15 or less.

Illustrative examples of the aliphatic monoalcohol include n-propanol, n-butanol, isobutyl alcohol, n-pentanol, 2-methyl-n-butanol, n-hexanol, 2-methyl-n-pentanol, 3-methyl-n-pentanol, 4-methyl-n-pentanol, 2,3-dimethyl-n-butanol, 3,3-dimethyl-n-butanol, 2-ethyl-n-butanol, n-heptanol, 2-methyl-1-hexanol, n-octanol, 4-methyl-1-heptanol, 5-methyl-1-heptanol, 6-methyl-1-heptanol, 3,5-dimethyl-1-hexanol, 4,5-dimethyl-1-hexanol, 2-ethyl-1-hexanol, n-nonanol, 2-methyl-1-octanol, 6-methyl-1-octanol, 7-methyl-1-octanol, 3,5,5-trimethyl-1-hexanol, n-decanol, 3,7-dimethyl-1-octanol, 2-ethyl-1-octanol, n-undecanol, n-dodecanol, n-tridecanol, n-tetradecanol, n-pentadecanol, n-hexadecanol, 2-hexyl-1-decanol, n-heptadecanol, n-octadecanol, 8-methyl-2-(4-methylhexyl)-1-decanol, 2-octyl-1-decanol, 5,7,7-trimethyl-2-(1,3,3-trimethylbutyl)-1-octanol, n-nonadecanol, n-eicosanol and 5,9-dimethyl-2-(1,5-dimethylhexyl)-1-decanol.

These alcohols may be used singly or two or more may be used in combination. However, from the standpoint of obtaining a single dimerized product in a good yield, it is preferable to use these alcohols singly.

In particular, in the preparation method of the invention, because, as mentioned above, the dimerization reaction proceeds in a good yield even when a branched aliphatic monoalcohol is used as the starting material, of the alcohols mentioned above, it is preferable to use a branched aliphatic monoalcohol, and especially preferable to use 3,5,5-trimethyl-1-hexanol.

The base used in the preparation method of the invention may be suitably selected from among inorganic bases and organic bases hitherto used in the Guerbet reaction.

Illustrative examples of inorganic bases include alkali metal hydroxides such as LiOH, NaOH, KOH, RbOH and CsOH; alkali metal carbonates such as $Li_2CO_3$, $Na_2CO_3$, $K_2CO_3$, $Rb_2CO_3$ and $Cs_2CO_3$; and alkali metal bicarbonates such as $LiHCO_3$, NaHCO3, $KHCO_3$, $RbHCO_3$ and CsHCO3.

Illustrative examples of organic bases include alkali metal alkoxides such as sodium methoxide, sodium ethoxide, sodium tert-butoxide, potassium methoxide, potassium ethoxide, and potassium tert-butoxide; alkali metal acetates such as sodium acetate and potassium acetate; pyridine compounds such as pyridine, 4-methylpyridine and N,N-dimethylaminopyridine; and tertiary amines such as triethylamine, triisopropylamine and 1,5-diazabicyclo[2.2.2]octane.

These bases may be used singly or two or more may be used in combination.

Of these, in order to have the dehydrogenation reaction and aldol condensation reaction proceed efficiently, a base having a relatively strong basicity is preferred. Alkali metal hydroxides such as LiOH, NaOH, KOH, RbOH and CsOH, and alkali metal alkoxides such as sodium methoxide, sodium ethoxide, sodium tert-butoxide, potassium methoxide, potassium ethoxide and potassium tert-butoxide are more preferred. In terms of such considerations as flexibility and cost, KOH, sodium methoxide and potassium tert-butoxide are even more preferred.

The base is used in an amount with respect to the monoalcohol which, although not particularly limited, is preferably from 0.01 to 20 mol %, more preferably from 0.1 to 15 mol %, and even more preferably from 0.5 to 10 mol %.

The catalyst used may also be one that is suitably selected from among those hitherto used in the Guerbet reaction. Exemplary catalysts include metal oxides, mixed metal oxides, transition metal complexes, carbonyl compounds, hydrogenation catalysts, apatite and hydrotalcite. In this invention, metal oxides and carbonyl compounds are preferred.

Illustrative examples of metal oxides include zinc oxide, magnesium oxide, lead oxide and nickel oxide. Zinc oxide is preferred.

The carbonyl compound is preferably an aliphatic aldehyde, with an aldehyde having a skeleton and a number of carbon atoms that correspond to the aliphatic monoalcohol used as the starting material being especially preferred.

Here, the "aldehyde compound having a skeleton and number of carbon atoms that correspond to the aliphatic monoalcohol" means the same thing as the aldehyde obtained by oxidizing the aliphatic monoalcohol. For example the aldehyde having a skeleton and number of carbon atoms that correspond to 3,5,5-trimethyl-1-hexanol is 3,5,5-trimethyl-1-hexanal.

The amount of catalyst used varies according to the type thereof and so cannot be strictly specified. However, the catalyst can be used in an amount of from about 0.01 to about 20 mol %, and preferably from 0.1 to 15 mol %, with respect to the monoalcohol.

In particular, the use of from 0.1 to 5 mol % is preferred in the case of metal oxides, and the use of from 5 to 15 mol % is preferred in the case of aldehyde compounds.

In order for the alcohol dehydrogenation reaction to proceed well, the reaction temperature used is generally at least 150° C., preferably at least 180° C., and more preferably at least 200° C. To suppress decomposition of the product, the upper limit is preferably not more than 280° C., and more preferably not more than 250° C.

In this invention, the "reaction temperature" refers to the external temperature (such as the oil bath temperature). In this case, the internal temperature at the beginning of the reaction is close to the boiling point of the monoalcohol used, although this gradually rises as the reaction proceeds, with the internal temperature at the end of the reaction normally reaching the boiling point of the target substance or, in cases where the boiling point is higher than the outside temperature, reaching close to the outside temperature.

The reaction time, which is not particularly limited, is generally from about 1 to about 20 hours, and preferably from about 1 to about 10 hours.

In the inventive method of preparation, the yield of the target substance can be further increased by carrying out the reaction while removing water formed by the reaction.

The method of removing water is not particularly limited, and may be any of the following: dehydration by physical adsorption, dehydration by phase separation using a Dean-Stark apparatus, and dehydration by chemical adsorption.

Physical adsorption methods are exemplified by methods which use synthetic zeolite such as molecular sieves.

Chemical adsorption methods are exemplified by methods which use a compound having a dehydrating action, such as magnesium sulfate or sodium sulfate.

Use can also be made of a substance such as silica gel having both a chemical adsorption action and a physical adsorption action.

In cases where dehydration is to be carried out by physical adsorption and chemical adsorption, dehydration may be effected by adding the dehydrating agent to be used to the reaction system. However, to dehydrate more efficiently and increase the reaction efficiency, as when using a Dean-Stark apparatus, it is preferable to use a method of dehydration which adsorbs, outside of the reaction system, steam generated under heating during the reaction or water that forms from condensation of the steam.

The Guerbet reaction is carried out without using a solvent, although a reaction solvent may be optionally used to adjust the viscosity of the reaction system or to facilitate dehydration treatment.

When a solvent is used, any solvent may be used provided it has a boiling point that allows the temperature of the system to rise up to the target reaction temperature and does not exert an adverse influence on the reaction. Examples of such solvents include N,N-dimethylformamide, N,N-dimethylacetamide, N-methyl-2-pyrrolidone, N-methyl-2-piperidone, tetramethylurea, dimethylsulfoxide, hexamethylphosphoramide, mineral spirits and tetralin. These may be used singly or two or more may be used in admixture.

Following reaction completion, a known work-up is carried out, after which the pure target substance can be obtained by a known method of purification such as distillation.

EXAMPLES

Working Examples and Comparative Examples are given below to more concretely illustration the invention, although the invention is not limited by these Examples. The measuring instruments used were as follows.

(1) Gas Chromatography-Mass Spectroscopy (GC-MS)
  Instrument: GC3800-1200L, from Bruker Daltonics, Ltd.
  Column: Agilent J&W GC column HP-INNOWax (length, 30 m; ID, 0.32 mm; film thickness, 0.25 μm), from Agilent Technology KK
  Injection amount: 1.0 μL
  Injection port temperature: 250° C.
  Column temperature: 40° C. (5 minutes), temperature rise to 250° C. at 20° C./min, 250° C. (7 minutes)
(2) GC (Gas Chromatography)
  Instrument: Agilent 6890N Network GC, from Agilent Technology KK
  Detector: FID
  Column: Agilent J&W GC column HP-INNOWax (length, 30 m; ID, 0.32 mm; film thickness, 0.25 μm), from Agilent Technology KK
  Injection amount: 1.0 μL
  Injection port temperature: 250° C.
  Column temperature: 40° C. (5 minutes), temperature rise to 250° C. at 20° C./min, 250° C. (7 minutes)

The abbreviations used are explained below.
  DOL: 1-decanol (from Tokyo Chemical Industry Co., Ltd.)
  DAL: decanal (Junsei Chemical Co., Ltd.)
  TMHOL: 3,5,5-trimethyl-1-hexanol (Tokyo Chemical Industry Co., Ltd.)
  TMHAL: 3,5,5-trimethylhexanal (Wako Pure Chemical Industries, Ltd.)
  OOL: 1-octanol (Wako Pure Chemical Industries, Ltd.)
  OAL: octanal (Wako Pure Chemical Industries, Ltd.)
  MS4A: molecular sieve 4A (Wako Pure Chemical Industries, Ltd.)

Working Example 1

A 100 mL flask equipped with a condenser packed at the bottom with MS4A was charged with 25.7 g of TMHOL as the starting material, 1.00 g (10 mol % with respect to the starting material) of potassium hydroxide (KOH) (granular; guaranteed reagent from Wako Pure Chemical Industries, Ltd.; purity, ≥85%) as the base, and 2.5 g (9.9 mol % with respect to the starting material) of TMHAL as the catalyst. Next, the mixture was reacted for 5 hours in an oil bath set to 230° C. while blowing (bubbling) 0.1 L/min of hydrogen gas (compressed hydrogen gas, from Toho Sakata Suiso KK) into the mixture under stirring. The mixture was then cooled to room temperature (about 23° C.), and the blowing of hydrogen gas was stopped.

The product peak retention time was confirmed by GC to agree with the retention time for the reference material. The peak portion was then analyzed by GC-MS, and the molecular weight and degradation product pattern were confirmed to agree with those for the reference material. The reaction product obtained was the target substance 2-(4,4-dimethylpentan-2-yl)-5,7,7-trimethyl-1-octanol, and the yield was 90.5%.

As used herein, the "yield" means the ratio of the amount of target product actually obtained to the amount of target product that can be obtained from the entire charged amount of the starting material, and is a value determined by the following formula.

Yield (%)=amount of target product (mol)/amount of starting material charged (mol)×2×100

Working Example 2

Aside from using 0.30 g (2.1 mol % based on the starting material) of zinc oxide (ZnO) (powder; guaranteed reagent from Junsei Chemical Co., Ltd.; purity, ≥99.0%) instead of TMHAL as the catalyst and setting the reaction time to 2 hours, the reaction was carried out in the same way as in Working Example 1. The reaction product was analyzed, whereupon the target substance was obtained and the yield was found to be 90.7%.

Working Example 3

Aside from using a Dean Stark apparatus equipped with a condenser (abbreviated below as "DS") instead of a condenser packed with MS4A, the reaction was carried out in the same way as in Working Example 1. The reaction product was analyzed, whereupon the target substance was obtained and the yield was found to be 89.0%.

Working Examples 4 to 8, Comparative Examples 1 to 10

Using the starting materials, bases and catalysts indicated in Table 1 below, reaction was carried out under the conditions shown in Table 1, following which analysis in the same way as in Working Example 1 confirmed that the target reaction product was obtained.

TABLE 1

|  |  | Starting material | (g) | Base | (g) | Catalyst | (g) | $H_2$ (L/min) | dehydration method | Reaction temp. (° C.) | Reaction time (hrs) | Yield (%) |
|---|---|---|---|---|---|---|---|---|---|---|---|---|
| Working Example | 1 | TMHOL | 25.70 | KOH | 1.00 | TMHAL | 2.50 | 0.1 | MS4A | 230 | 5 | 90.5 |
|  | 2 | TMHOL | 25.70 | KOH | 1.00 | ZnO | 0.30 | 0.1 | MS4A | 230 | 2 | 90.7 |
|  | 3 | TMHOL | 25.70 | KOH | 1.00 | TMHAL | 2.50 | 0.1 | DS | 230 | 5 | 89.0 |
|  | 4 | TMHOL | 25.70 | KOH | 1.00 | ZnO | 0.30 | 0.1 | DS | 230 | 5 | 100.0 |
|  | 5 | DOL | 29.70 | KOH | 1.10 | DAL | 2.94 | 0.1 | DS | 260 | 5 | 91.6 |
|  | 6 | DOL | 28.00 | KOH | 0.99 | ZnO | 0.29 | 0.1 | DS | 260 | 5 | 82.9 |
|  | 7 | OOL | 24.60 | KOH | 1.05 | OAL | 2.42 | 0.1 | DS | 230 | 5 | 81.2 |
|  | 8 | OOL | 22.90 | KOH | 0.99 | ZnO | 0.29 | 0.1 | DS | 230 | 5 | 92.9 |
| Comparative Example | 1 | TMHOL | 25.70 | KOH | 1.00 | TMHAL | 2.50 | — | MS4A | 230 | 4 | 83.8 |
|  | 2 | TMHOL | 25.70 | KOH | 1.00 | ZnO | 0.30 | — | MS4A | 230 | 4 | 55.5 |
|  | 3 | TMHOL | 25.70 | KOH | 1.00 | TMHAL | 2.50 | — | DS | 230 | 6 | 60.7 |
|  | 4 | TMHOL | 25.70 | KOH | 1.00 | ZnO | 0.30 | — | DS | 230 | 6 | 60.4 |
|  | 5 | TMHOL | 25.70 | KOH | 1.00 | TMHAL | 2.50 | — | — | 230 | 5 | 24.0 |
|  | 6 | TMHOL | 25.70 | KOH | 1.00 | ZnO | 0.30 | — | — | 230 | 5 | 12.0 |
|  | 7 | DOL | 29.70 | KOH | 1.10 | DAL | 2.94 | — | DS | 260 | 5 | 65.2 |
|  | 8 | DOL | 28.00 | KOH | 0.99 | ZnO | 0.29 | — | DS | 260 | 5 | 61.9 |
|  | 9 | OOL | 24.60 | KOH | 1.05 | OAL | 2.42 | — | DS | 230 | 5 | 75.5 |
|  | 10 | OOL | 22.90 | KOH | 0.99 | ZnO | 0.29 | — | DS | 230 | 5 | 62.9 |

As shown in Table 1, the yield of the target substance was higher in Working Examples 1 to 8 in which the reaction was carried out by blowing in hydrogen gas than in the Comparative Examples in which hydrogen gas was not blown in.

The invention claimed is:

1. A method for preparing a branched alcohol, comprising:
   providing a mixture comprising an aliphatic monoalcohol having five or more carbon atoms, a base comprising at least one member selected from the group consisting alkali metal hydroxides and alkali metal alkoxides, and a catalyst comprising at least one member selected from the group consisting of metal oxides and carbonyl compounds; and
   subjecting said mixture to a dimerizing reaction, wherein the dimerizing reaction is carried out under atmospheric pressure and while blowing hydrogen gas into said mixture.

2. The branched alcohol preparation method of claim 1, wherein the blowing of the hydrogen gas into the mixture is carried out by inserting a blowing tube into the mixture and bubbling hydrogen gas through the mixture.

3. The branched alcohol preparation method of claim 1, wherein the aliphatic monoalcohol is an aliphatic monoalcohol having eight or more carbon atoms.

4. The branched alcohol preparation method of claim 1, wherein the aliphatic monoalcohol is a branched aliphatic monoalcohol.

5. The branched alcohol preparation method of claim 1, wherein a hydrogen gas blowing rate is about 0.05 to 25 L/min per mole of the monoalcohol.

6. The branched alcohol preparation method of claim 1, wherein the dimerizing reaction temperature is the range of 150° C. to 250° C.

7. The branched alcohol preparation method of claim 1, wherein the aliphatic monoalcohol is 1-octanol, 1-decanol or 3,5,5-trimethyl-1-hexanol.

8. The branched alcohol preparation method of claim 4, wherein the branched aliphatic monoalcohol is 3,5,5-trimethyl-1-hexanol.

9. The branched alcohol preparation method of claim 1, wherein the reaction is carried out while removing water that forms in the dimerization reaction.

10. The branched alcohol preparation method of claim 9, wherein the removal of water is carried out by dehydration by physical adsorption, dehydration by phase separation using a Dean-Stark apparatus, or dehydration by chemical adsorption.

11. The branched alcohol preparation method of claim 10, wherein the removal of water is carried out by dehydration by physical adsorption or dehydration by phase separation using a Dean-Stark apparatus.

12. The branched alcohol preparation method of claim 1, wherein the catalyst is a metal oxide.

13. The branched alcohol preparation method of claim 3, wherein the catalyst is a metal oxide.

14. The branched alcohol preparation method of claim 4, wherein the catalyst is a metal oxide.

15. The branched alcohol preparation method of claim 7, wherein the catalyst is a metal oxide.

16. The branched alcohol preparation method of claim 1, wherein the catalyst is an aliphatic aldehyde.

17. The branched alcohol preparation method of claim 1, wherein the catalyst is an aliphatic aldehyde having a skeleton and a number of carbon atoms corresponding to the aliphatic monoalcohol.

18. The branched alcohol preparation method of claim 3, wherein the catalyst is an aliphatic aldehyde having a skeleton and a number of carbon atoms corresponding to the aliphatic monoalcohol.

19. The branched alcohol preparation method of claim 4, wherein the catalyst is an aliphatic aldehyde having a skeleton and a number of carbon atoms corresponding to the aliphatic monoalcohol.

20. The branched alcohol preparation method of claim 7, wherein the catalyst is an aliphatic aldehyde having a skeleton and a number of carbon atoms corresponding to the aliphatic monoalcohol.

* * * * *